United States Patent
Borrello

(10) Patent No.: US 11,389,608 B2
(45) Date of Patent: Jul. 19, 2022

(54) METHODS AND SYSTEMS FOR PATIENT AIRWAY AND LEAK FLOW ESTIMATION FOR NON-INVASIVE VENTILATION

(71) Applicant: KONINKLIJKE PHILIPS N.V., Eindhoven (NL)

(72) Inventor: Michael Anthony Borrello, Carlsbad, CA (US)

(73) Assignee: Koninklijke Philips N.V., Eindhoven (NL)

(*) Notice: Subject to any disclaimer, the term of this patent is extended or adjusted under 35 U.S.C. 154(b) by 732 days.

(21) Appl. No.: 16/333,646

(22) PCT Filed: Sep. 13, 2017

(86) PCT No.: PCT/EP2017/072979
§ 371 (c)(1),
(2) Date: Mar. 15, 2019

(87) PCT Pub. No.: WO2018/050676
PCT Pub. Date: Mar. 22, 2018

(65) Prior Publication Data
US 2019/0255271 A1    Aug. 22, 2019

Related U.S. Application Data

(60) Provisional application No. 62/396,427, filed on Sep. 19, 2016.

(51) Int. Cl.
*A61M 16/00* (2006.01)
*A61M 16/06* (2006.01)

(52) U.S. Cl.
CPC ...... *A61M 16/026* (2017.08); *A61M 16/0051* (2013.01); *A61M 16/0066* (2013.01);
(Continued)

(58) Field of Classification Search
CPC .............. A61M 16/026; A61M 16/021; A61M 16/022; A61M 16/024; A61M 16/0051;
(Continued)

(56) References Cited

U.S. PATENT DOCUMENTS

| 6,557,553 B1 | 5/2003 | Borrello |
| 2007/0157930 A1 | 7/2007 | Soliman et al. |

(Continued)

FOREIGN PATENT DOCUMENTS

| EP | 1270036 A2 | 1/2003 |
| EP | 2368593 A1 | 9/2011 |

(Continued)

OTHER PUBLICATIONS

Borrello:"Modeling and Control of Systems for Critical Care Ventilation"; 2005 American Control Conference, Jun. 2005, pp. 2166-2180.

*Primary Examiner* — Joseph D. Boecker
*Assistant Examiner* — Brian T Khong
(74) *Attorney, Agent, or Firm* — Daniel H. Brean

(57) ABSTRACT

A method (800) for estimating patient airway flow in a non-invasive ventilator system includes: (i) determining (830) an estimated gas flow; (ii) determining (840) a proximal pressure error value; (iii) compensating (850) for the determined proximal pressure estimate error value; (iv) compensating (854) for an error in the estimated gas flow; (v) determining (856) an estimated gas flow leak; (vi) monitoring (860) on a breath to breath basis for a leak; (vii) determining (870) a gas flow leak factor; (viii) adjusting (880) the estimated gas flow leak; (ix) detecting (872) a bias on the airway flow estimate; (x) determining (874) that the system is within a quiescent state of a breath; (xi) de-biasing (976) the estimated gas flow to drive the bias to near zero;
(Continued)

and (xii) suspending (878) breath to breath bias correction on an immediately subsequent breath.

15 Claims, 11 Drawing Sheets

(52) U.S. Cl.
CPC ..... *A61M 16/06* (2013.01); *A61M 2016/0027* (2013.01); *A61M 2016/0039* (2013.01); *A61M 2205/15* (2013.01); *A61M 2205/3331* (2013.01); *A61M 2205/50* (2013.01)

(58) Field of Classification Search
CPC .......... A61M 16/0003; A61M 16/0066; A61M 16/0069; A61M 2016/0027; A61M 2016/003; A61M 2016/0033; A61M 2016/0036; A61M 2016/0039; A61M 2016/0042; A61M 2016/0015; A61M 2016/0018; A61M 2205/14; A61M 2205/15; A61M 2205/18; A61M 2205/3331; A61M 2205/3334; A61M 2205/3337; A61M 2205/3341; A61M 2205/3344

See application file for complete search history.

(56) References Cited

U.S. PATENT DOCUMENTS

| | | | |
|---|---|---|---|
| 2009/0241951 A1* | 10/2009 | Jafari | A61M 16/06 128/204.21 |
| 2012/0215081 A1 | 8/2012 | Euliano et al. | |
| 2012/0247471 A1* | 10/2012 | Masic | A61M 16/026 128/204.23 |
| 2012/0304997 A1* | 12/2012 | Jafari | A61M 16/0051 128/204.23 |
| 2013/0167842 A1* | 7/2013 | Jafari | A61M 16/026 128/204.21 |
| 2014/0053840 A1 | 2/2014 | Liu | |
| 2015/0000665 A1 | 1/2015 | Isaza | |
| 2015/0107584 A1* | 4/2015 | Jafari | A61M 16/0063 128/202.22 |
| 2015/0144130 A1* | 5/2015 | O'Donnell | A61M 16/0051 128/202.22 |
| 2016/0114115 A1* | 4/2016 | Glenn | G16H 40/63 128/204.23 |

FOREIGN PATENT DOCUMENTS

| | | |
|---|---|---|
| WO | 9806449 A1 | 2/1998 |
| WO | 2010099373 A1 | 9/2010 |
| WO | 2012004718 A1 | 1/2012 |
| WO | 2012004733 A1 | 1/2012 |

* cited by examiner

METHODS AND SYSTEMS FOR PATIENT AIRWAY AND LEAK FLOW ESTIMATION FOR NON-INVASIVE VENTILATION

CROSS-REFERENCE TO PRIOR APPLICATIONS

This application is the U.S. National Phase application under 35 U.S.C. § 371 of International Application No. PCT/EP2017/072979, filed on Sep. 13, 2017, which claims the benefit of U.S. Provisional Patent Application No. 62/396,427, filed on Sep. 19, 2017. These applications are hereby incorporated by reference herein.

FIELD OF THE INVENTION

The present disclosure is directed generally to methods and systems for estimating patient airway flow and leak flow utilizing remote ventilator pressure and flow sensors in a non-invasive ventilator system.

BACKGROUND

The most common means of providing critical care ventilation requires intubating patients with an endotracheal tube that seals within the trachea using an inflatable cuff. Intubation offers the best means of clinically managing the airway and maintaining lung inflation, but it introduce significant risks including tissue abrasion, infection, and sedation of the patient due to extreme discomfort. Accordingly, intubation is appropriately called 'invasive' ventilation, and the clinician's decision to intubate must be carefully considered. For a select group of hospitalized patients requiring breathing support, the risks leading to adverse side effects of intubation can outweigh the benefits.

In light of significant risks of invasive ventilation, a new approach was adopted from home care ventilation that offers the benefit of applying support through the airway, but uses a connection that simply involves fitting a mask over the patient's mouth and nose or uses a tracheostomy tube. This approach is called non-invasive positive pressure ventilation, or simply non-invasive ventilation ("NIV"). For NIV, some leak is expected and often purposely introduced in order to reduce end-tidal $CO_2$ that would otherwise be rebreathed by the patient, since a single limb circuit connects the ventilator to the mask in an NIV system. In comparison, invasive ventilation uses a dual-limb connecting circuit that separately carries exhaled gases, which prevents rebreathing of $CO_2$ in invasive ventilation which therefore requires no leak.

Although the primary function of a ventilator is to provide or supplement patient breathing, ventilators typically include integral monitoring and alarm functions to safeguard the patient and provide essential clinical information. In order to provide these functions, the ventilator monitors waveforms including pressure, flow, and volume. To avoid excess tubing and wires near the patient, and to reduce the risk of occluding the airway with patient secretions, it is desirable not to use an airway flow sensor. Without a proximal flow sensor, sensors inside the ventilator can be used to monitor flow. However, the four to six feet of tubing that separate the ventilator and patient create significant issues with these sensors. Pressure-flow dynamics of the connecting tube, including leak, account for different flow at the patient airway compared to what is measured at the ventilator. Tubing resistance and compliance tend to smooth flow transient, and leak leads to loss of flow at the patient's airway. As a result, flow at the ventilator is a poor estimate of airway flow.

To account for the effect of resistance and compression, ventilator manufacturers apply filtering to waveform measurements using a patient circuit model. These models typically call for the differentiation of the measured pressure, which tends to amplify high frequency noise in the pressure input signal. And since these filters do not involve lung mechanics, the model is incomplete and the airway flow estimate is even more inaccurate.

Accordingly, there is a need in the art for non-invasive ventilator systems that properly estimate patient airway flow and leak flow utilizing remote ventilator pressure and flow sensors.

SUMMARY OF THE INVENTION

The present disclosure is directed to inventive methods and systems for estimating patient airway flow in a non-invasive ventilator system. Various embodiments and implementations herein are directed to a non-invasive ventilator system that calculates a highly accurate estimate of patient airway flow and of unknown leak flow. The non-invasive ventilator uses a feedback mechanism to minimize the difference between measured proximal pressure and estimated proximal pressure, where the estimated proximal pressure is generated using a model of the patient circuit that connects the ventilator with the patient. The non-invasive ventilator also compensates for leaks that can occur in the system by adjusting a known leak flow estimate.

Generally in one aspect, a method for estimating patient airway flow in a non-invasive ventilator system is provided. The method includes the steps of: (i) providing a non-invasive ventilator system having tubing with a distal, ventilator end and a proximal, patient end; (ii) obtaining a measurement of tubing compliance and a measurement of one or more parameters of an exhalant port leak flow model of the non-invasive ventilator system; (iii) measuring, using one or more distal gas flow sensors of the non-invasive ventilator, gas flow at the distal end of the tubing; (iv) measuring, using a proximal pressure sensor of the non-invasive ventilator, pressure at the proximal end of the tubing; (v) determining an estimated gas flow at the proximal end of the tubing, the estimated gas flow calculated from the measurement of gas flow at the distal end of the tubing, the measurement or pressure at the proximal end of the tubing, the obtained measurement of tubing compliance, and the obtained measurement of one or more parameters of the leak flow model; (vi) determining a proximal pressure error value by subtracting the measured pressure at the proximal end of the tubing from the estimated pressure at the proximal end of the tubing; (vii) compensating, using a compensator, for the determined proximal pressure estimate error value; (viii) compensating for an error in the estimated gas flow at the proximal end of the tubing by feeding that estimate back into a sum of accumulated flows; (ix) determining an estimated gas flow leak, the estimated gas flow leak calculated from the estimated pressure at the proximal end of the tubing and the obtained measurement of one or more parameters of the leak flow model; (x) monitoring for an unknown leak in the non-invasive ventilator system; (xi) determining, when an unknown leak is identified on a breath to breath basis, a gas flow leak factor; (xii) adjusting, with the determined gas flow leak factor on a breath to breath basis, the estimated gas flow leak; (xiii) detecting a bias on the airway flow estimate; (xiv) determining that the system is within a quiescent state of a breath; (xv) de-biasing, if the system is in the quiescent state, the estimated gas flow leak factor to drive the bias to zero; and (xvi) suspending breath to breath bias correction on an immediately subsequent breath.

According to an embodiment, the step of determining that the system is within a quiescent state comprises determining that the breath is in an exhalation phase, that the airway flow estimate is greater than 3 lpm, that the proximal pressure is constant, and that the gas flow is constant.

According to an embodiment, the de-biasing occurs in less than approximately 300 milliseconds.

According to an embodiment, the step of obtaining a measurement of tubing compliance and a measurement of one or more parameters of the leak flow model includes one or more calibration measurements.

According to an embodiment, the method further includes the step of comparing the gas flow leak factor to a predetermined lower limit.

According to an embodiment, an alarm is triggered if the gas flow leak factor is below the predetermined lower limit.

According to an embodiment, the method further includes the step of comparing the gas flow leak factor to a predetermined upper limit.

According to an embodiment, an alarm is triggered if the gas flow leak factor is above the predetermined upper limit.

According to an embodiment, the compensator is a proportional-integral compensator.

Generally, in one aspect, a non-invasive ventilator system is provided. The system includes: airway tubing having a distal, ventilator end and a proximal, patient end; a distal gas flow sensor configured to measure gas flow at the distal end of the tubing; a proximal pressure sensor configured to measure pressure at the proximal end of the tubing; and a gas flow controller configured to supply a determined volume of gas to the distal end of the tubing, wherein the gas flow controller is configured to determine the supplied volume of gas by: (i) determining an estimated gas flow at the proximal end of the tubing, the estimated gas flow comprising a measurement of gas flow at the distal end of the tubing, a measurement of pressure at the proximal end of the tubing, a measurement of tubing compliance, and a measurement of one or more parameters of a leak flow model; (ii) determining a proximal pressure error value by subtracting a measured pressure at the proximal end of the tubing from the estimated pressure at the proximal end of the tubing; (iii) compensating for the determined proximal pressure estimate error value; (iv) compensating for an error in the estimated gas flow at the proximal end of the tubing by feeding that estimate back into a sum of accumulated flows; (v) determining an estimated gas flow leak, the estimated gas flow leak comprising the estimated pressure at the proximal end of the tubing and the obtained measurement of one or more parameters of the leak flow model; (vi) monitoring for an unknown leak in the non-invasive ventilator system; (vii) determining, when an unknown leak is identified on a breath by breath basis, a gas flow leak factor; (viii) adjusting, with the determined gas flow leak factor on a breath to breath basis, the estimated gas flow leak; (ix) detecting a bias on the airway flow estimate; (x) determining that the system is within a quiescent state of a breath; (xi) de-biasing, if the system is in the quiescent state, the estimated gas flow leak factor to drive the bias to zero; and (xii) suspending breath to breath bias correction on an immediately subsequent breath.

According to an embodiment, the controller includes a compensator configured to compensate for the determined proximal pressure estimate error value.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a non-invasive ventilator ("NIV") system and method. More generally, Applicants have recognized and appreciated that it would be beneficial to provide an NIV that accurately estimates patient airway flow and leak flow utilizing remote ventilator pressure and flow sensors. For example, the NIV uses feedback control to minimize the difference between measured and estimated proximal pressure, where the estimated pressure is synthesized using a model of the patient circuit that connects the ventilator with the patient. Unexpected or unknown leaks that occur during use are compensated using a feedback mechanism that modifies net flow to zero by adjusting a known leak estimate. The method and system results in an airway flow estimate that closely tracks true airway flow with low noise and minimum bias, and provides an accurate estimate of the unknown leak flow.

Although the method and system described below is applied to an NIV, the methods could similarly be utilized to manage the movement of compressible gas through any conveying channel, such as for heating and/or air conditioning systems. Essentially any system that contains a need to remotely estimate flow could utilize the methods and systems described or otherwise envisioned herein.

Figure 1:
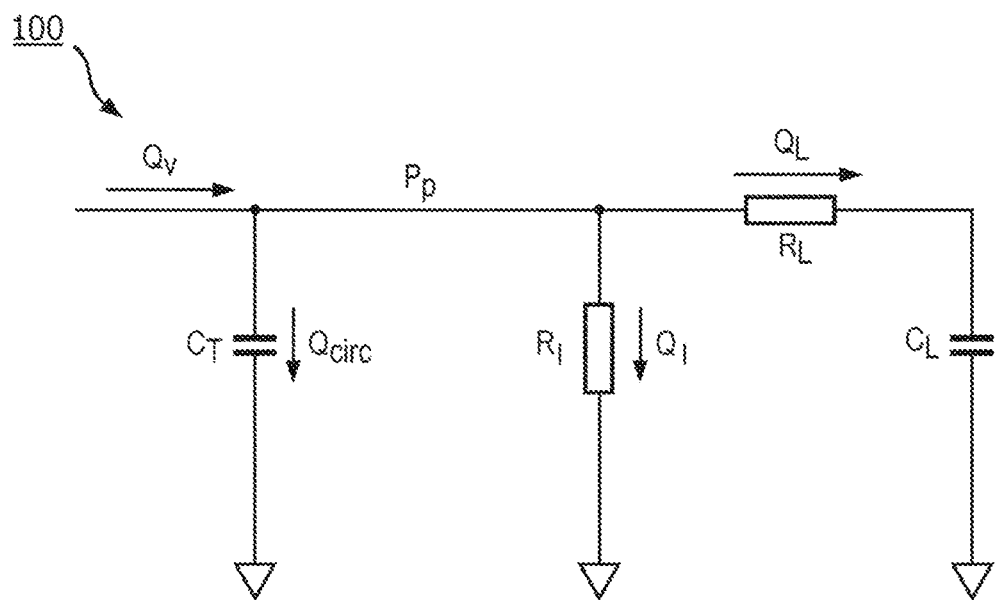
FIG. 1 is a schematic representation modeling flows and pressures in a patient-connected non-invasive ventilator system, in accordance with an embodiment.

Referring to FIG. 1, in accordance with an embodiment, is a model 100 for an NIV system using an electrical circuit analogy where branch currents represent flows, nodal voltages represent pressures, capacitance represents pneumatic compliance, and electrical resistance, flow restriction. In FIG. 1, $Q_v$ is the measured net flow into tubing from the ventilator; $C_T$ is the measured compliance of the tubing; $Q_{circ}$ is the flow component stored in tubing compliance during compression; $P_p$ or $P_{prox}$ is the measured pressure at the proximal side of the airway; $R_l$ is the measured Port leak resistance; $Q_l$ is the flow component lost to ambient through the port leak; $Q_L$ is the unknown flow component into the lung; $R_L$ is the unknown nonlinear lumped airway resistance; and $C_L$ is the unknown lumped compliance of the lung. The set of equations that model the circuit in FIG. 1 and relate pressures and flows, if interpreted directly for a solution of the lung flow result in a non-causal form requiring that the noisy proximal pressure signal be differentiated. But then the patient circuit is not in isolation, but rather coupled to the patient's lung which, if these dynamics are considered, results in a smoothing of the derivative. The coupled model depicted in FIG. 1 also results in tangling between circuit and lung parameters, which is not difficult to untangle in estimation if the system was linear, but the nonlinear resistance parameters makes untangling impossible—the resulting quadratic differential equation is intractable and so the lung resistance and compliance cannot be estimated by typical means.

Figure 3:
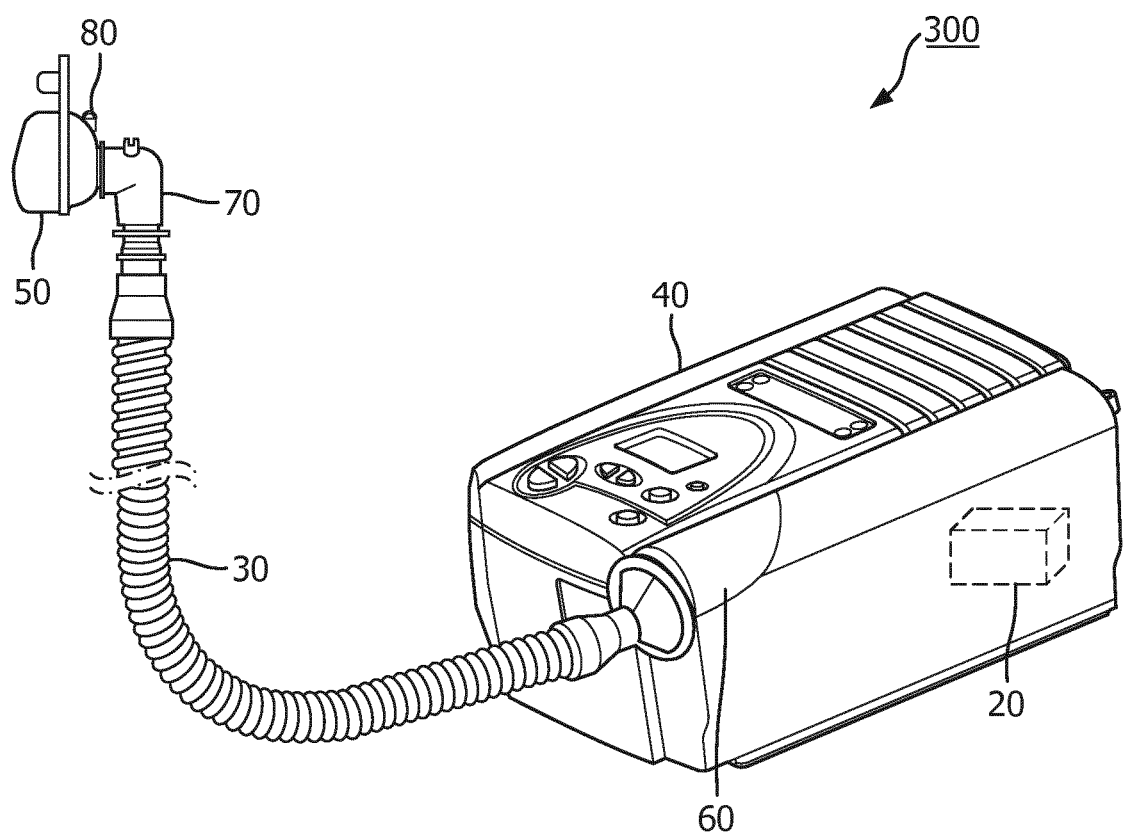
FIG. 3 is a schematic representation of a non-invasive ventilator system in accordance with an embodiment.

In view of the foregoing, various embodiments and implementations are directed to an NIV that estimates patient airway flow and leak flow with feedback mechanisms that utilize remote ventilator pressure and flow sensors. Referring to FIG. 3, in one embodiment, is a representation of an example NIV system 300. The NIV includes a gas source which can be any gas utilized for breathing, including but not limited to atmospheric air and oxygen, among others. The gas source is expelled from the NIV with a predetermined pressure. The NIV also includes a controller 20, which is a conventional microprocessor, an application specific integrated circuit (ASIC), a system on chip (SOC), and/or a field-programmable gate arrays (FPGA), among other types of controllers. A controller may be implemented with or without employing a processor, and also may be implemented as a combination of dedicated hardware to perform some functions and a processor (e.g., one or more programmed microprocessors and associated circuitry) to perform other functions.

The controller 20 can be coupled with or otherwise in communication with any needed memory, power supply, I/O devices, control circuitry, and/or other devices necessary for operation of the NIV according to the embodiments described or otherwise envisioned herein. For example, in various implementations, a processor or controller may be associated with one or more storage media. In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The NIV includes a tube or tubing 30 that delivers gas from the remote ventilator component 40 to the user interface 50. User interface 50 can be, for example, a face mask that covers all or a portion of the user's mouth and/or nose. There may be masks of many different sizes to accommodate patients or individuals of different sizes, and/or the mask may be adjustable. As another alternative, user interface 50 may fit within or on, or otherwise interact with, a tracheostomy tube. Accordingly, the user interface 50 may be a variety of sizes to accommodate tracheostomies of different shapes and sizes. The user interface is configured to fit with at least a portion of the patient's airway and includes an exhalation port 80. The NIV system comprises a distal gas flow sensor 60 at the end of the tubing near the remote ventilator component 40, and a proximal pressure sensor 70 at the end of the tubing near the user interface 50. Either of distal gas flow sensor 60 or proximal pressure sensor 70 may comprise, for example, two or more sensors. For example, distal gas flow sensor 60 can comprise a blower flow sensor and an $O_2$ valve sensor. Further, any of the sensors may be external or internal to the NIV. Controller 20 is configured to receive sensor data from both distal gas flow sensor 60 and proximal pressure sensor 70, either through wired or wireless communication.

Notably, proximal pressure sensor 70 is located at the output of tubing 30 rather than in close proximity to the patient or individual's mouth. Accordingly, the data obtained by proximal pressure sensor 70 is not directly equivalent to gas flow in the patient airway, and an estimate of airway flow is necessary. One method used to estimate patient airway flow ($Q_L$) is via the following equation:

$$\hat{Q}_L = Q_v - C_T \frac{dP_p}{dt} - \text{sgn}(P_p)\sqrt{\left|\frac{P_p}{R_l}\right|} \qquad (1)$$

where $\hat{Q}_L$ is estimated patient airway flow, $Q_v$ is the gas flow as measured by the distal gas flow sensor 60, $C_T$ is the patient connecting circuit compliance, $P_p$ is the gas flow as measured by the proximal pressure sensor 70, and $R_l$ is the total leak resistance. However, equation (1) results in a noisy airway flow estimate and large transient errors. This is largely due to the second term in the equation which accounts for flow lost to compression of gas in the patient circuit and the derivative of a noisy pressure signal. To compensate for noise the estimate is usually filtered, but this leads to additional error if the filter is not selected correctly to match patient lung dynamics.

Figure 2:
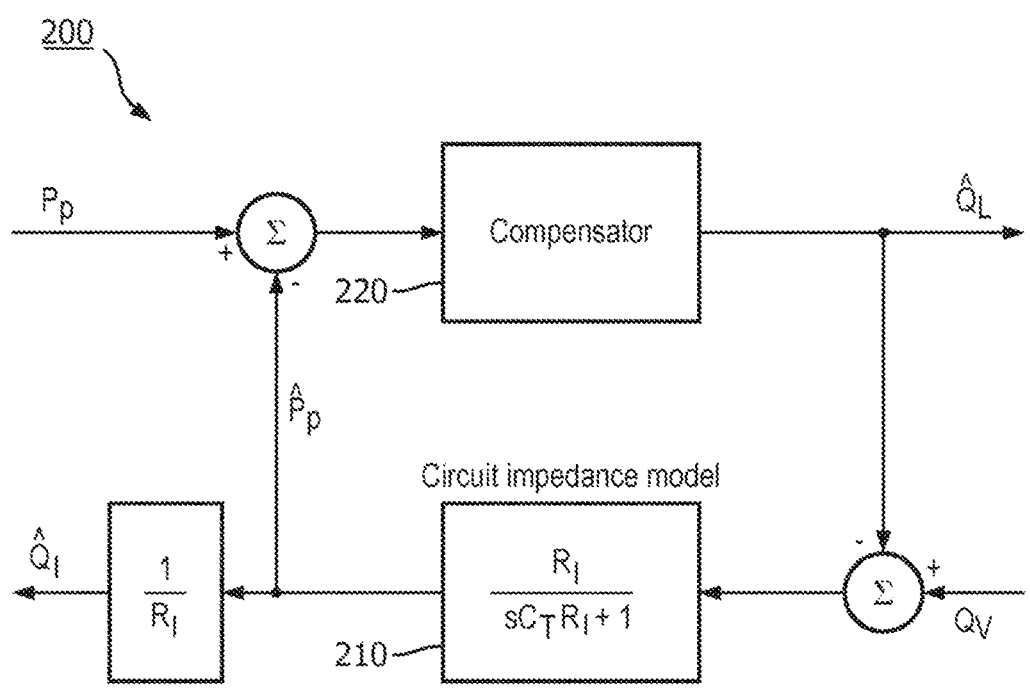
FIG. 2 is a schematic representation of a model for estimating patient airway flow in a non-invasive ventilator system, in accordance with an embodiment.

Referring to FIG. 2, in one embodiment, is a schematic of a ventilator/patient circuit 200 for estimating patient airway flow in a non-invasive ventilator system. The circuit comprises a measured distal gas flow $Q_v$ which is the gas flow input into the circuit, a circuit impedance model 210 which uses measures of the leak resistance and circuit compliance to the gas flow, an estimate of $Q_l$ which is the connecting circuit leak flow (which utilizes the total leak resistance $R_l$), the proximal pressure $P_p$ as measured by the proximal pressure sensor 70, a compensator 220, and the estimated patient airway flow $\hat{Q}_L$. According to an embodiment, the pressure synthesized by the connecting circuit impedance model 210 is an estimate of the proximal pressure based on a sum of net flows into the circuit impedance. This is subtracted from the measured pressure and the difference between measured and estimated pressures is minimized by the controller 20. By choosing a suitable compensator 220, the controller output is effectively driven to approach a close estimate of the airway flow ($\hat{Q}_L$) to complete a feedback loop. According to an embodiment, a proportional-integral compensator ("PI compensator") is utilized to drive the difference between the proximal pressure measurement and its estimate to zero and thus the estimates of the airway and leak flows. According to an embodiment, the PI compensator utilizes the following equation:

$$\hat{Q}_L = \left(\frac{K_i + K_P s}{s}\right)(P_p - \hat{P}_p) \quad (2)$$

where $K_i$ is the integral gain and $K_p$ the proportional gain. Although a PI compensator can be utilized, many other compensators that provide loop stability and suitably cause the error to converge towards zero—therefore causing $\hat{P}_p$ to track $P_p$ can similarly be used.

Airway Flow Analysis

According to an embodiment, therefore, the NIV model in FIG. 1 can be expanded to a nonlinear, linear parameter varying model. The nonlinear equations that approximate the coupled NIV-patient circuit with the patient are then:

$$P_{prox} = \frac{1}{C_T}\int(Q_v - Q_l - Q_L)dt \quad (3)$$

$$P_{prox} - P_L = R_L Q_L^2 \mathrm{sgn}(Q_L) \quad (4)$$

$$P_{prox} = R_l Q_l^2 \mathrm{sgn}(Q_l) \quad (5)$$

$$P_L = \frac{1}{C_L}\int Q_L dt \quad (6)$$

Figure 4:
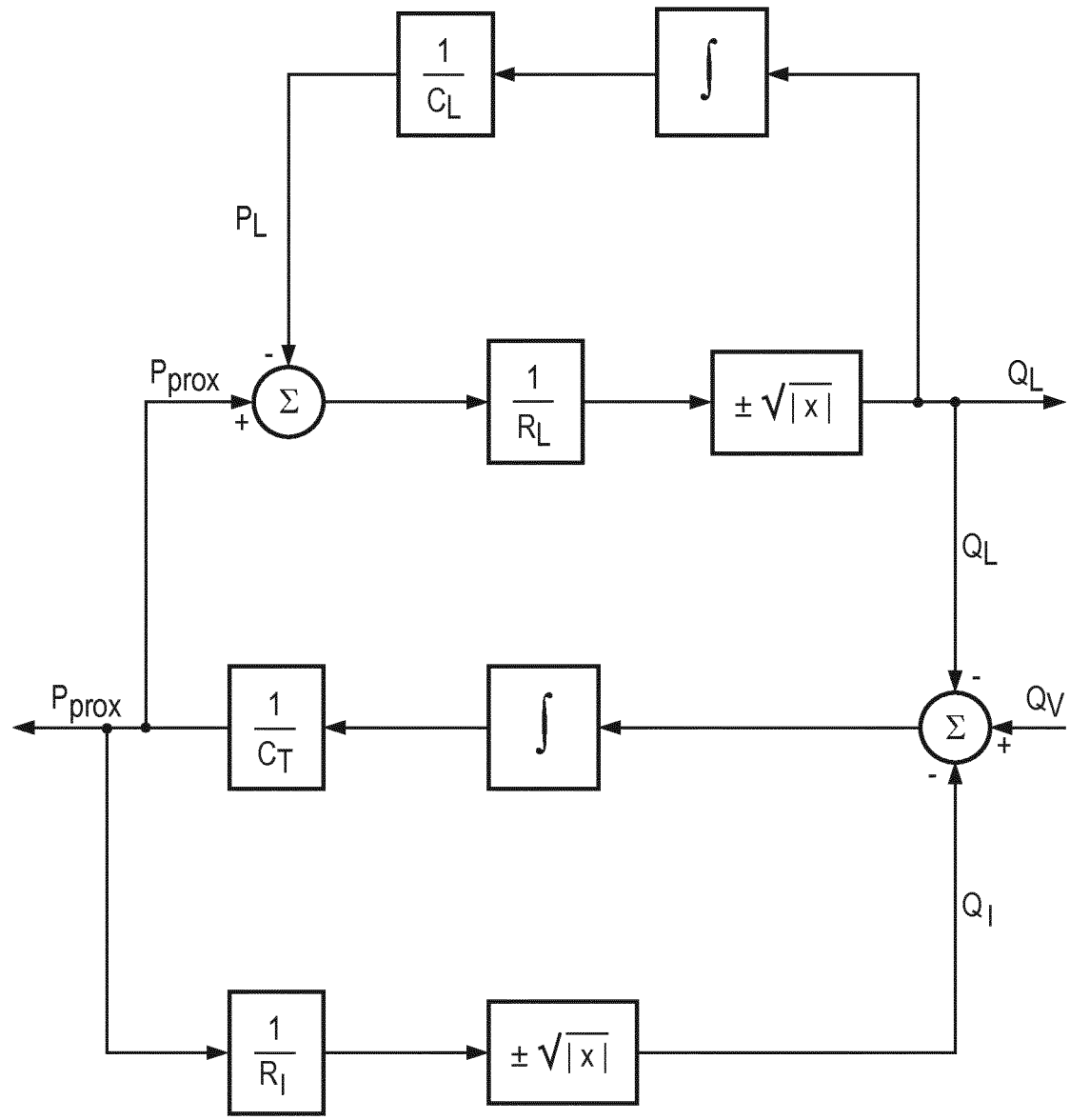
FIG. 4 is schematic representation modeling flows and pressures in a patient-connected non-invasive ventilator system, in accordance with an embodiment.

This set of equations can be expressed as a block diagram, as illustrated in FIG. 4. The upper portion of FIG. 4 depicts the portion of the model involving the lung, and the lower portion of FIG. 4 depicts the patient circuit. The two portions couple to one another through the proximal pressure, $P_{prox}$ and lung flow, $Q_L$. If patient circuit resistance is not considered the ventilator outlet flow only can be used as a measureable input, and the machine pressure offers no further useful information. $Q_1$ is the net leak flow, determined by $P_{prox}$ and the leak flow model (shown as, for example, $R_1$ in FIG. 4, although other models are possible). The output to determine is $Q_L$. Although $Q_L$ is not measured, the proximal airway pressure, $P_{prox}$ is measured. $P_L$ is the lung pressure, and $C_L$ and $R_L$ are the lung compliance and resistance respectively. It is typically assumed that both $C_T$ and the leak model are known, and according to one embodiment can be determined from a pre-use calibration procedure on the circuit, among other mechanisms.

Figure 5:
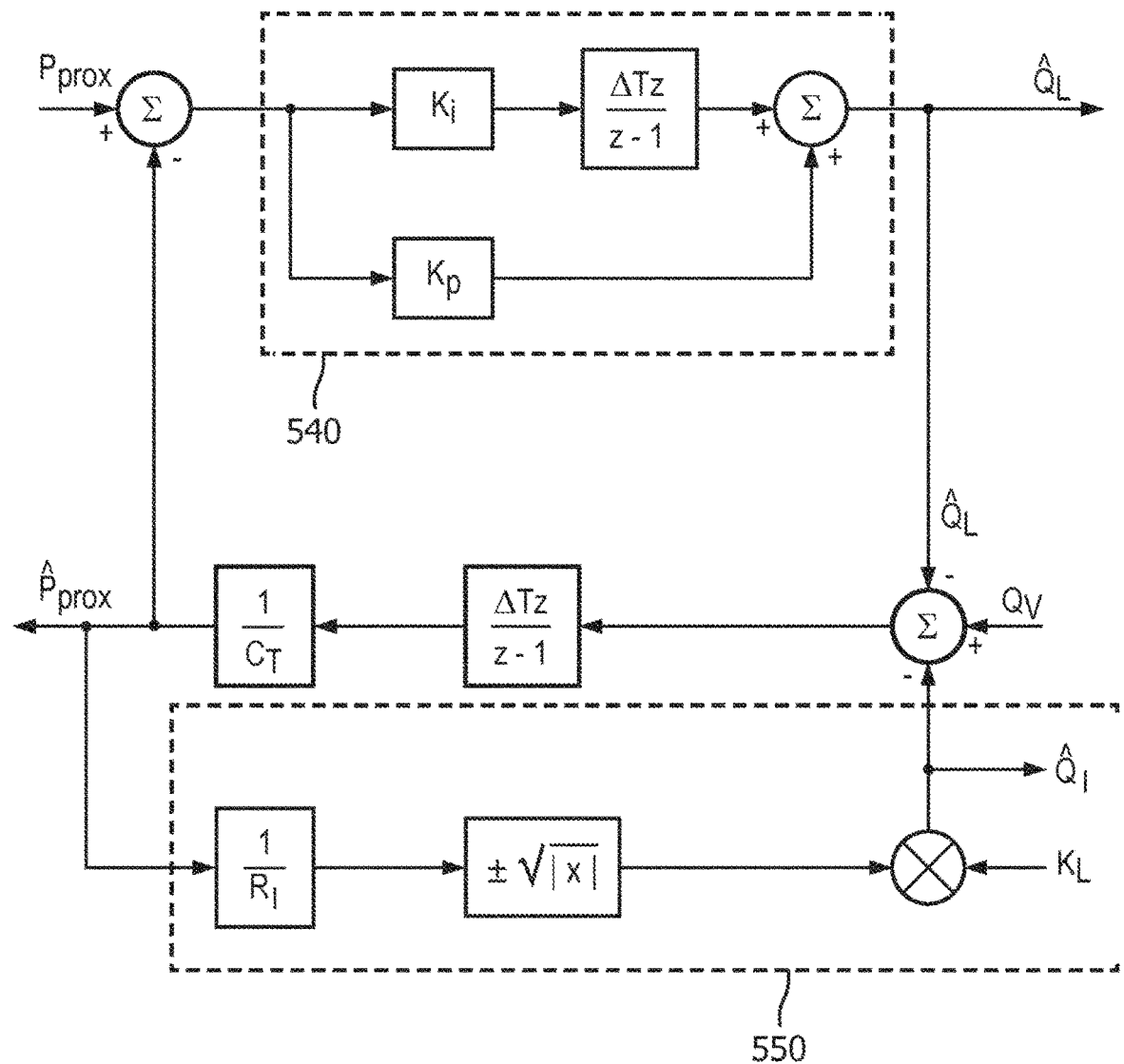
FIG. 5 is schematic representation of a model for estimating patient airway flow in a non-invasive ventilator system, in accordance with an embodiment.

According to an embodiment, since there is difficulty in determining $R_L$ and $C_L$, this part of the model can be eliminated and replaced by a discrete time filter if other adjustments are also made. Additionally, the known part of the model can be replaced by a discrete time equivalent of the original continuous time model as illustrated in FIG. 5. The filter replaces the portion of the model depicted in FIG. 4 that represented the lung, but it does not simulate the lung. The output of the circuit portion of the model that determines $P_{prox}$ is now treated as an estimate of $P_{prox}$ ($\hat{P}_{prox}$), and this value is subtracted from the actual measured $P_{prox}$. This difference, e, becomes the input to the filter. The integral action of the filter acts to minimize e, by the action of its output that acts on the circuit part of the model, feeding back into where $Q_L$ once connected. But $Q_L$ is now treated as an estimate and so designated as $\hat{Q}_L$. By selecting the filter parameters $K_i$ and $K_p$, the overall feedback system can be stabilized and e can be made to converge to zero. With rapid convergence, $\hat{P}_{prox}$ will track the measured $P_{prox}$ and this will cause $\hat{Q}_L$ and $\hat{Q}_l$ to track the actual lung and leak flow (provided the actual $R_1$ is correct).

Leak Disturbance Compensator

When unknown or unexpected leaks occur within the NIV system, additional control is required in order to ensure convergence of the estimated leak and lung flows. Although no further information can be derived on a sample by sample basis while pressure or flow is changing, there is information over a full breath cycle that can be used to determine if there is unexpected leak flow in the circuit-lung system. Any leak flow not accounted for in the known leak components of the system can appear as bias on the airway flow estimate. Furthermore, structural differences in the various leaks that comprise the total leak can be better managed if they are separately modeled rather than lumped together in a single leak model.

Assuming that ventilator settings are fixed for a set of breaths, the physical volume that enters the lung during inhalation should equal the volume that exits the lung during exhalation. Considering how the estimator accounts for flow, it can be assumed under most conditions that any difference between the two volumes estimated (by integrating the airway flow estimate both in and out) can be attributed to volume loss not accounted for by the fixed leak model. The fixed leak model includes components such as port and mask leak.

To compensate for unknown leak, the leak flow estimate in the estimator of FIG. 4 can be corrected using a multiplying factor over the breath cycle. But to accommodate possible differences in structure, the system is first modified to partition the various leak component models. And furthermore the correction factor need only be applied to the unknown component of leak. This approach of a separate, breath-to-breath controller assumes that the unknown leak is somewhat stationary over the period of a breath cycle or is at least changing slowly. It also assumes that the magnitude of the unknown leak can be reliably measured, which requires integrating the estimated airway flow over the full breath (i.e., net volume). This may be equivalent to, for example, measuring the inhaled and exhaled volumes and subtracting one from the other. The net volume should be zero when the bias has been removed. Any residual leak appears as bias on the airway flow estimate.

Figure 6:
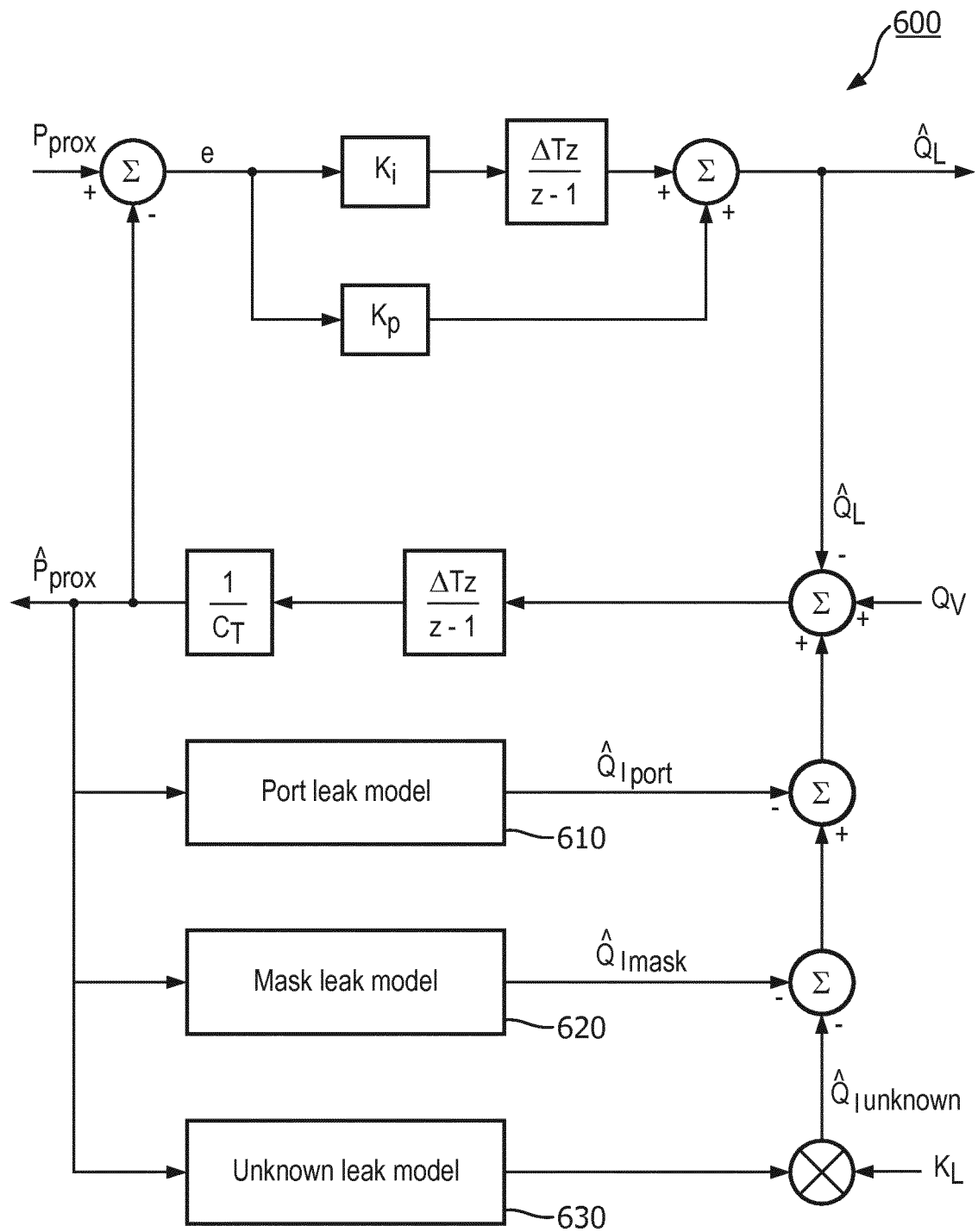
FIG. 6 is a schematic representation of a model for compensating for unknown leak in a non-invasive ventilator system, in accordance with an embodiment.

Referring to FIG. 6, in one embodiment, is a model 600 comprising an estimator modified to compensate for unknown leak. The leak correction factor, $K_L$, which is updated at the start of every breath and is based on reconciliation of leak from the prior breath, multiplies the output of the unknown leak to get $\hat{Q}_{l\ unknown}$ before feeding back into the estimator. The sum of the port leak 610, the mask leak 620, and the breath-to-breath corrected unknown leak 630 becomes the total leak and removes bias from the airway flow estimate.

The manner in which $K_L$ is determined requires careful consideration of how the net breath volume is processed since there is a one (1) breath delay involved, and improper design can lead to unpredictable behavior and instability in the estimator. But a more critical factor is that sensitivity of $K_L$ to changes in timing and pressure can significantly change the loop gain—according to those different operating conditions. Changes in loop gain can lead to wildly different convergence rates or worse, instability in the form of limit cycles or latched flow.

To provide consistent sensitivity, the net (estimated lung) volume, $V_L(k)$ is first reduced to a net 'average' bias flow, $\overline{Q}_L(k)$ by dividing $V_L(k)$ by the breath interval, $T_B(k)$ and secondly by dividing $\overline{Q}_L(k)$ (assumed affected by total leak) by the average known leak flow which is estimated according to an average leak flow based on known leak resistance. But the unequal pressures during inhalation and exhalation can also change the average flow. To compensate, average pressure is factored in. The result leads to a unit-less airway flow bias metric, $\tilde{Q}_L(k)$, with a constant sensitivity of unity regardless of breath settings or load. By normalizing the net volume in this manner, the effective value of K for controller design becomes unity for all cases.

Figure 7:
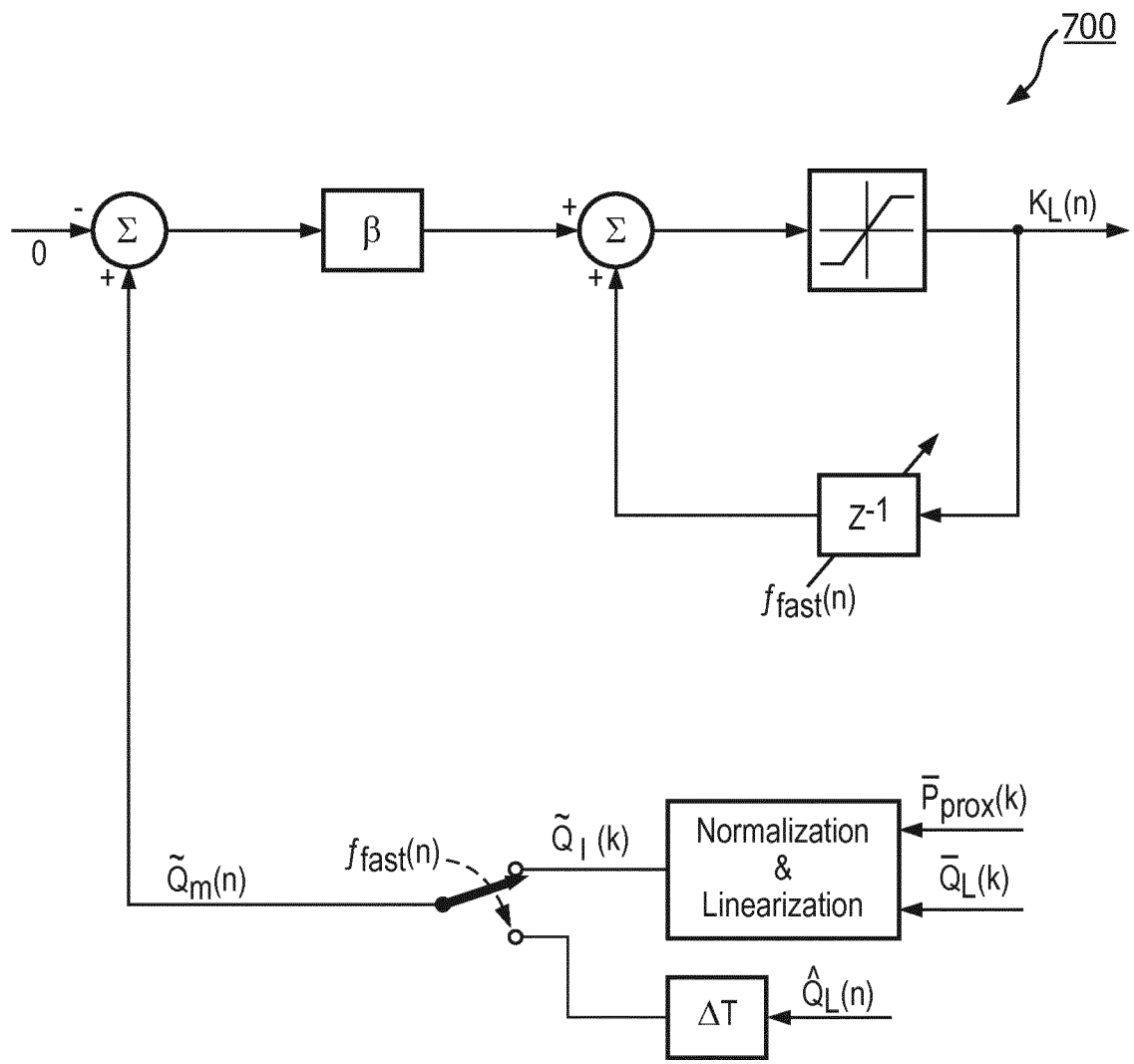
FIG. 7 is a schematic representation of a model for determining an unknown leak factor in a non-invasive ventilator system, in accordance with an embodiment.

Referring to FIG. 7, in one embodiment, is a model of a controller 700 for determining the unknown leak factor based on airway flow estimate bias estimation. The bias metric estimator is shown in the feedback path of the controller that determines the leak correction factor. The leak correction factor is limited between bounded values for leak on the high side and leak obstruction or mask mismatch on the low end. If there is no leak flow beyond what is expected from the mask and exhalation port, the output of the controller should converge to a number very close to zero. By allowing the correction factor to go lower than 0, the controller can correct for known leak flow resistances that were under-estimated, or if for any reason the port leak or mask leak were to become occluded during operation.

Breath to breath correction for disturbance leak is effective in steady state operation when the size of bias is small, enabling the patient to trigger. But for start-up, changes in the breath settings, and for large sudden leaks that can cause the net breath volume to become significantly large, the bias can reach a high level that locks the patient out from being able to trigger a breath. Triggering is necessary for breath to breath bias correction. In such situations the estimator output can be stuck in exhalation with a large bias. To address this problem, the disturbance leak controller is further equipped with an algorithm that detects the situation and provides rapid de-biasing to a level at which triggering can resume. Basically the following consistent conditions all must be satisfied for this fast de-biasing maneuver to occur: (i) the ventilator phase must be exhalation; (ii) the magnitude of the of the airway flow estimate must be >3 lpm; (iii) the proximal pressure must be flat; and (iv) the ventilator flow must be flat.

Given these conditions, the breath is considered to be in a quiescent state which permits a rapid de-biasing of the estimator. The leak factor is rapidly changed until the airway flow estimate is driven close to zero. This mechanism is more likely to be triggered with IE ratios much smaller than one. Hysteresis is used in this control to avoid rapid switching between the states. Since rapid de-biasing for the current breath will upset the net volume calculation for the current breath, breath to breath bias correction based on the net volume is suspended for the subsequent breath. The combined action of fast de-biasing generally eliminates bias due to sudden leak events in a single breath.

Figure 8A:
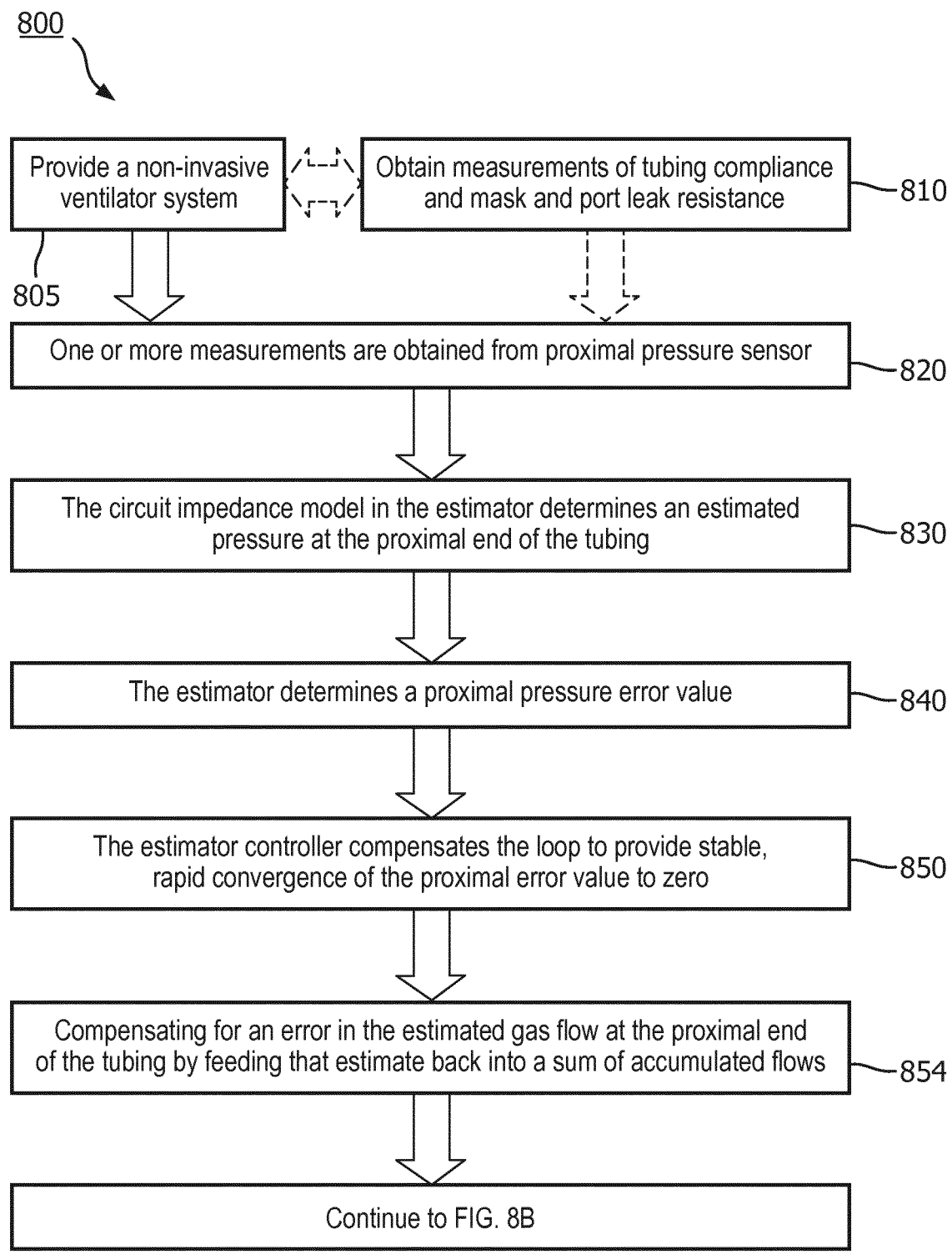
FIG. 8A is a flowchart of a method for estimating patient airway flow in a non-invasive ventilator system, in accordance with an embodiment.
Figure 8B:
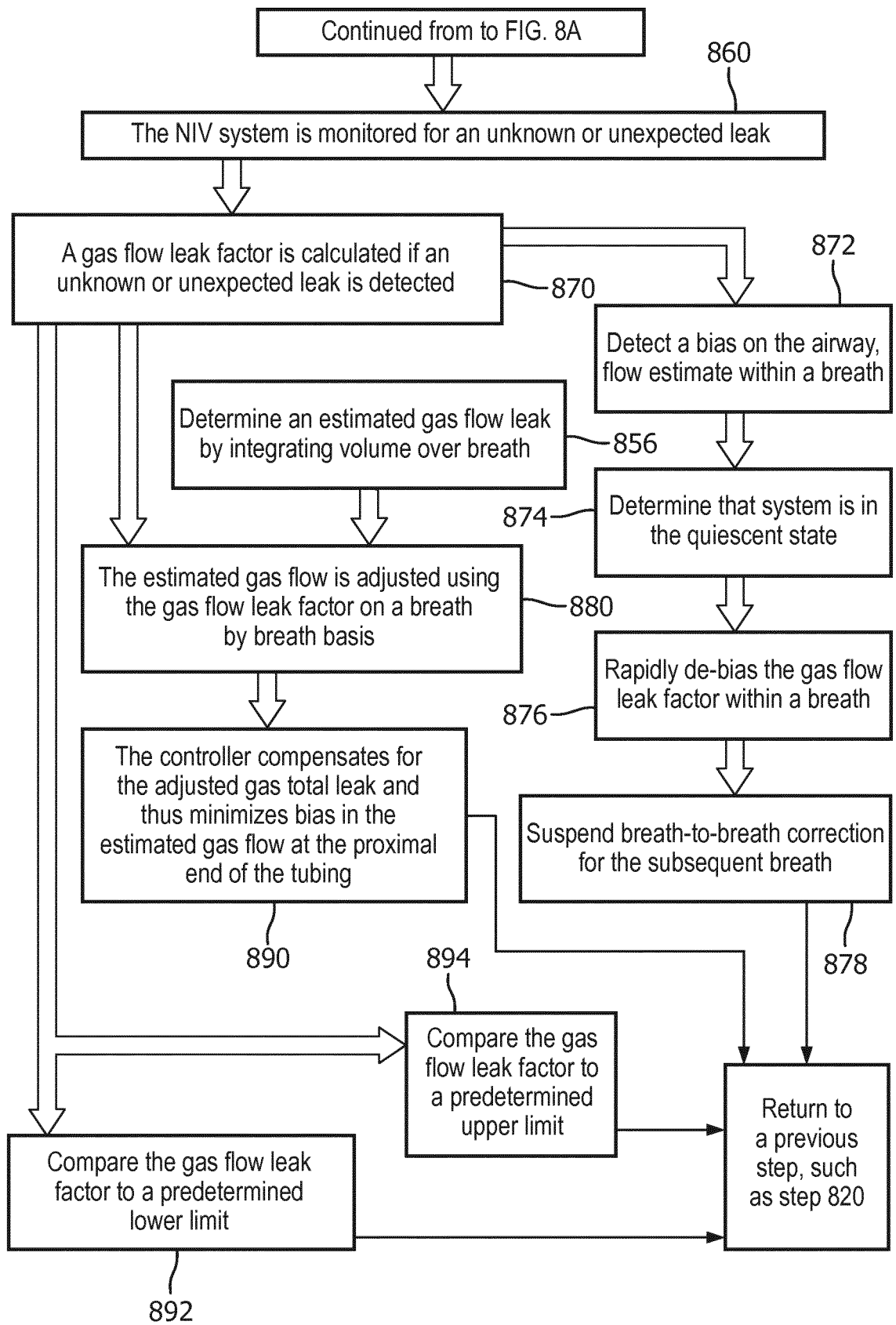
FIG. 8B is a flowchart of a method for estimating patient airway flow in a non-invasive ventilator system, in accordance with an embodiment.

Referring to FIGS. 8A and 8B, in one embodiment, is a flowchart of a method 800 for estimating patient airway flow in a non-invasive ventilator system. At step 805, an NIV system is provided. The NIV system can be any of the embodiments described or otherwise envisioned herein. At step 810, measurements of tubing compliance ($C_T$) and leak resistance ($R_1$) are retrieved or obtained. These measurements are typically obtained during patient setup prior to breath delivery. For example, according to one embodiment the value of $R_1$ is determined based on a calibration procedure. Alternatively, $R_1$ can be retrieved from a database of $R_1$ values, where the values can depend on the user selecting tubing set and/or port leak part numbers from a user screen interface, automatically using an RFID tag implanted in the tubing set or its components, a bar scanning system that reads the part numbers into the ventilator, or a variety of other methods. Tubing compliance ($C_T$), for example, affects the amount of gas compressed in the ventilator circuit according to the pressure generated by the ventilator throughout the breath. The compressible volume can vary depending on the internal volume of the circuit and stiffness of its wall.

At step 820 of the method, one or more measurements are obtained from proximal pressure sensor 70 at the end of the tubing proximal the user interface 50. The proximal pressure sensor 70 can obtain the measurement(s) of pressure using any of a variety of measurement methods and devices.

At step 830 of the method, the controller 20 determines an estimated pressure ($P_{prox}$) at the proximal end of the tubing. Estimation of pressure at the proximal end of the tubing utilizes one or more obtained measurements of gas flow ($Q_v$) at the distal end of the tubing, as well as the obtained measurement of tubing compliance ($C_T$) and leak resistance.

At step 840 of the method, the controller 20 determines a proximal pressure estimate error value (e) by subtracting the actual measured proximal pressure ($P_{prox}$) from estimated proximal pressure ($\hat{P}_{prox}$). At step 850 of the method, the controller 20 minimizes the pressure error using a proportional-integral compensator. As shown for example, in FIG. 5, according to an embodiment, the calculated difference e is utilized as an input to filter 540. The integral action of the filter acts to minimize e, by the action of its output that acts on the circuit part of the model, feeding back into where $Q_L$ once connected. But $Q_L$ is now treated as an estimate and so designated as $\hat{Q}_L$. By selecting the filter parameters $K_i$ and $K_p$ by either analytical methods or ad-hoc tuning, the overall feedback system can be stabilized and e can be made to rapidly converge and remain near zero. With the convergence, $\hat{P}_{prox}$ will track the measured $P_{prox}$ and this will cause $\hat{Q}_L$ and $\hat{Q}_l$ to track the actual lung and leak flow—provided the leak model, its parameters, and the compliance are correct. When additional 'unknown' leaks occur or $R_1$ was perhaps determined with an error, the system requires further control measures to assure convergence of the estimated leak and lung flows, and bias, as discussed in greater detail below. According to an embodiment, the measurements and/or calculations obtained throughout the course of the method can be obtained and/or updated periodically or continually. According to an embodiment, the leak disturbance model 550 in FIG. 5 calculates a correcting factor $K_L$ which can be utilized in whole or in part to correct the output of the leak model.

At step 854 of the method, the controller causes errors in the obtained estimate of the patient airway flow to become small by providing the estimate back into the sum of accumulated flows.

At step 856 of the method, an estimated gas flow leak is calculated. The estimated gas flow leak is based on the estimated pressure at the proximal end of the tubing and the leak model with parameters obtained apriori. Like several other steps of the method, this step can occur before, after, or simultaneously with other steps.

At step 860 of the method, the NIV system is monitored for an unknown or unexpected leak. The circuit impedance model described herein includes a leak model for estimating leak behavior, but this leak is intentionally built into the circuit, such as for patient exhalation through exhalation port 80. This leak value is assumed not to change, and is typically calibrated or known prior to patient connection. During the application of ventilation, additional unknown or unexpected leaks can develop, for example around the mask skirt sealing the mask against the patient's face. Unknown leak can be treated as disturbance in the system, and the size estimated during ventilation using a feedback controller that is the same or separate from controller 20. According to an embodiment, the feedback controller acts to minimize the integrated, estimated airway flow, $\hat{Q}_L$, over a full breath. This is equivalent to minimizing the net estimated lung volume for each breath. If net estimated lung volume is reduced to zero, there is no leak component in the average flow that was integrated to get the volume. Any residual volume acts in a breath-to-breath feedback control law to adjust a correcting factor, $K_l$, which corrects the output of the leak model.

Accordingly, at step 870 of the method, the gas flow leak factor $K_L$ is calculated and updated at the start of every breath and is based on reconciliation of leak from the prior breath. The leak correction factor multiplies the output of the unknown leak to get $\hat{Q}_{l\ unknown}$, before feeding back into the estimator.

At step 872 of the method, the system detects a large bias on the airway flow estimate. When the size of bias is small, the patient can trigger a breath and breath-to-breath correction for disturbance leak is effective. However, there are situations where bias reaches a sufficiently high level that locks the patient out from being able to trigger a breath, including at start-up, when there are changes in or to the breath settings, and/or when large sudden leaks cause the net breath volume to become significantly large. Without triggering, there cannot be breath-to-breath bias correction, and the estimator output may thus be stuck in exhalation. Accordingly, the system comprises a disturbance leak controller that detects a large bias on the airway flow estimate.

At step 874 of the method, the system determines whether the breath is in a quiescent state. The preferred quiescent state for large rapid de-biasing is during exhalation, when the patient is unlikely to trigger a breath and there is flat pressure and flat flow. However, any other period where the patient is unlikely to trigger a breath and there is flat pressure and flat flow would be suitable for large rapid de-biasing. Accordingly, the system determines that the breath is in the quiescent state and de-biasing is appropriate if each of the following criteria are satisfied: (1) the ventilator phase is exhalation; (2) the magnitude of the airway flow estimate is >3 lpm; (3) the proximal pressure is flat; and (4) the ventilator flow is flat. If those conditions are satisfied, then the system determines that the breath is in a quiescent state, and a de-biasing can occur.

At step 876 of the method, the system changes the gas flow leak factor in order to quickly de-bias the estimated airway flow to near zero. According to an embodiment, the fast de-bias occurs within 1 millisecond to 1 second, and preferably within 100 to 300 milliseconds. However, other de-bias periods can be determined and controlled by, for example, increasing or decreasing the loop gain. A rapid de-biasing is preferred, in order to reduce the probability that the patient will try to trigger a breath. Performing rapid de-biasing during a quiescent period such as exhalation also reduces the probability that the patient will try to trigger a breath.

At step 878 of the method, the system suspends breath-to-breath correction on the subsequent breath. Breath-to-breath corrections, also called between breath corrections, can normally be performed by the system between any two breaths. However, the breath-to-breath correction must be suspended immediately after a rapid de-biasing in order to avoid interfering with net volume integration, since the volume of the current breath will be in error due to the fast bias correction maneuver.

At step 880 of the method, the estimated gas flow is adjusted using the gas flow leak factor $K_L$, and at step 890 of the method, the controller 20 compensates for the adjusted gas total leak as described or otherwise envisioned herein.

At optional step 892 of the method, the gas flow leak factor is compared to a predetermined lower limit. If the gas flow leak factor is below the predetermined lower limit, then a low leak or fault condition of the exhalant port is determined. A warning, alarm, or gas flow adjustment can then occur depending on the settings and/or programming of the NIV system. The lower limit can be a factory setting, an adjustable setting, and/or a setting that depends on factors such as the patient's size, condition, illness, and more, among many other factors.

At optional step 894 of the method, the gas flow leak factor is compared to a predetermined upper limit. If the gas flow leak factor is above the predetermined upper limit, then a disconnect fault of the patient tubing is determined. A warning, alarm, or gas flow adjustment can then occur depending on the settings and/or programming of the NIV system. The upper limit can be a factory setting, an adjustable setting, and/or a setting that depends on factors such as the patient's size, condition, illness, and more, among many other factors. Among many other things, these limits can detect $CO_2$ build-up and a possible circuit disconnect.

Figure 9:
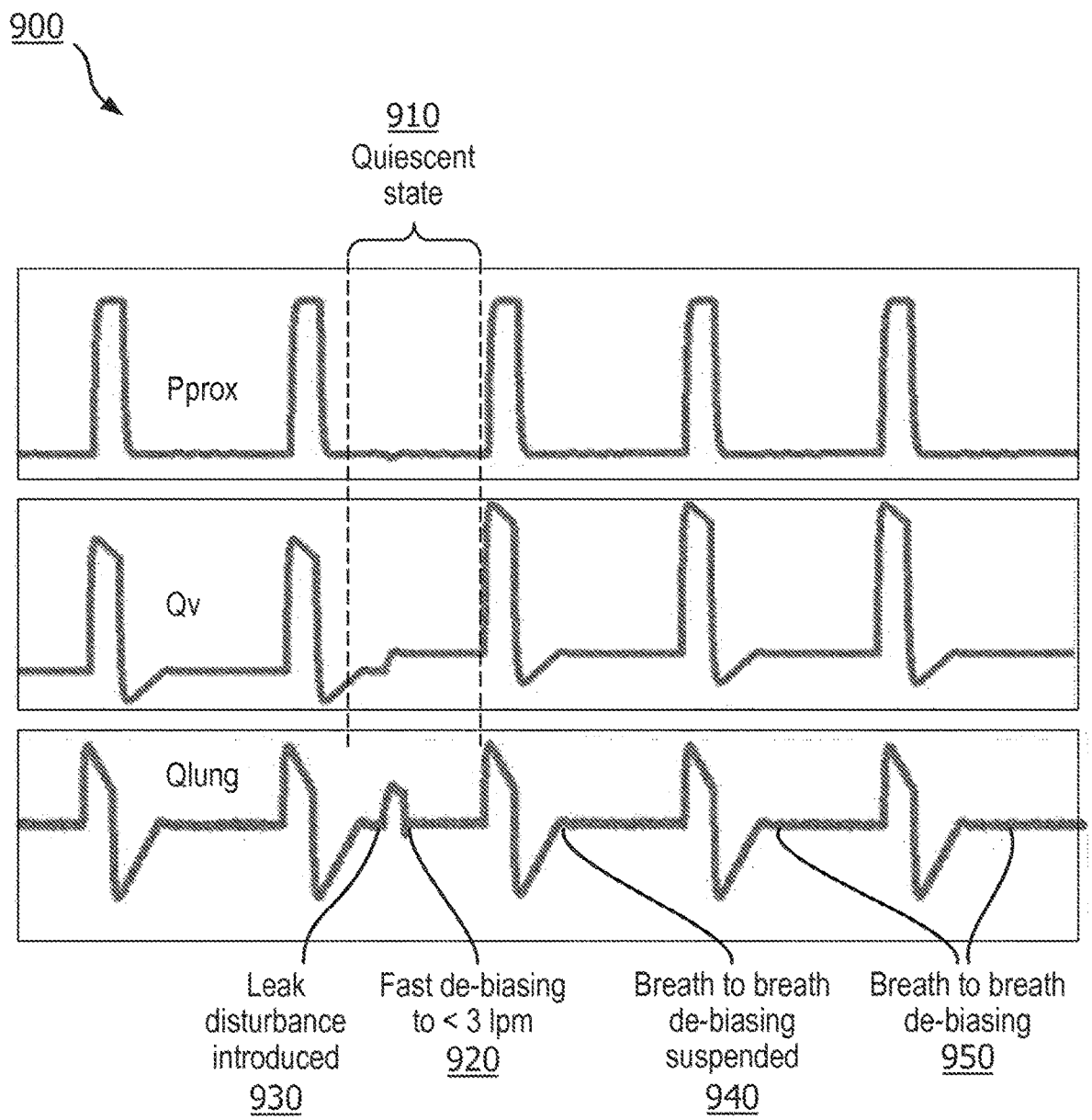
FIG. 9 is a graph of leak debiasing in a non-invasive ventilator system, in accordance with an embodiment.

Referring to FIG. 9, in one embodiment, is a graph 900 illustrating the action of fast de-biasing after a sudden leak is introduced on the second breath, in this example. As shown in FIG. 9, the graph includes a quiescent state 910. If the system determines that: (1) the ventilator phase is exhalation; (2) the magnitude of the airway flow estimate is >3 lpm; (3) the proximal pressure is flat; and (4) the ventilator flow is flat, then the system can perform a fast de-bias 920 to de-bias the estimated airway flow to near zero. The quick de-bias may be necessary, for example, due to a leak disturbance 930. De-biasing during the subsequent breath-to-breath period 940 is suspended, but can occur during one or more later between breath periods 950.

EXAMPLE

Estimator Calculations

Providing below are one possible embodiment of the systems and methods described or otherwise envisioned herein, including the system and method described or depicted in any of FIGS. 1-10. Many other embodiments in addition to those described below are possible.

According to an embodiment, the estimator comprises a filter that minimizes the difference between measured and estimated $P_{prox}$, and the circuit dynamic model section. The calculations can be updated every control cycle, although other time frames are possible. The filter section can comprise, for example, the following:

$$\hat{\epsilon}_{QL}(n) = -P_{prox}(n) + \hat{P}_{prox}(n) \quad (7)$$

$$I_{Fin}(n) = \hat{Q}_{LKi}\hat{\epsilon}_{QL}(n) - I_{Fout}(n) - \hat{Q}_{LKp}\hat{\epsilon}_{QL}(n) + \hat{Q}_L(n) \quad (8)$$

$$\hat{Q}_L(n) = \min\{\max\{(I_{Fout}(n) - \hat{Q}_{LKp}\hat{\epsilon}_{QL}(n)), Q_{Lmin}\}, Q_{Lmax}\} \quad (9)$$

$$I_{Fout}(n) = \begin{cases} 0 & \text{if } Q_{Lreset} = 1 \\ \Delta T \cdot I_{Fin}(n-1) + I_{Fout}(n-1) & \text{otherwise} \end{cases} \quad (10)$$

where, according to an embodiment, $I_{Fout}(0) = I_{Fin}(0) = 0$; $Q_{Lmin} = -5.0$ lps; $Q_{Lmax} = 5.0$ lps; $\hat{Q}_{LKi} = 10.0$ liters/(sec$^2$ cm H$_2$O); and $\hat{Q}_{LKp} = 0.3$ liters/(sec cm H$_2$O).

According to an embodiment, overall negative feedback is accomplished in the estimator loop no matter which order the difference between proximal pressure measure and estimate are taken. According to this embodiment, an odd number of negative signs are required in the loop. For example, when the pressure error is written as $P_{prox} - \hat{P}_{prox}$, the compensator equations must include a sign inversion since $\hat{Q}_L$ feeds back into the sum of flows with a negative sign. According to an embodiment, this negative feedback is required for stable estimator operation.

According to an embodiment, the estimator circuit dynamic model section can comprise, for example, the following:

$$Q_{sum}(n) = \frac{1}{60}(Q_b(n) + Q_{O2}(n)) - \hat{Q}_L(n) - \hat{Q}_l(n) \quad (11)$$

$$I_{Cin}(n) = Q_{sum}(n) + Q_{La}(n) \quad (12)$$

$$C_T = C_{Tcal} \quad (13)$$

$$Q_{La}(n) = \hat{P}_{prox}(n) - \frac{1}{C_T}I_{Cout}(n) \quad (14)$$

$$\hat{P}_{prox}(n) = \min\left\{\max\left\{\frac{1}{C_T}I_{Cout}(n), P_{proxMin}\right\}, P_{proxMax}\right\} \quad (15)$$

$$I_{Cout}(n) = \begin{cases} 0 & \text{if } Q_{Lreset}(n) = 1 \\ \Delta T \cdot I_{Cin}(n-1) + I_{Cout}(n-1) & \text{otherwise} \end{cases} \quad (16)$$

$$\hat{Q}_l(n) = K_L(k)[Q_{Lmask}(n) + Q_{Lport}(n)] \quad (17)$$

$$Q_{Lport}(n) = \frac{1}{2K_{2port}}\left(\sqrt{4.0K_{2port}\max\{0, \hat{P}_{prox}(n)\} + K_{1port}^2} - K_{1port}\right) \quad (18)$$

$$Q_{Lmask}(n) = \quad (19)$$

$$\begin{cases} 0 & \text{if } MaskLeakType = \text{'other'} \\ \sqrt{\left|\frac{\hat{P}_{prox}(n)}{R_{lmask}}\right|} * \text{sgn}(\hat{P}_{prox}(n)) & \text{otherwise} \end{cases}$$

According to an embodiment, equation (18) assumes that the port leak flow is always positive; the quadratic model assumes $\hat{P}_{prox}(n) > 0$ and therefore the model does not include sign correction. $K_L$, determined by the output of the unknown leak compensation controller is indexed by the breath rate (index k) and updated at the start of every breath. So its value reflects information from the previous breath, applied to the current breath.

The value of $R_{lmask}$ is known based on apriori calibration data of the mask and categorized according to MaskLeakType, which is selected during patient setup, prior to breath delivery. TABLE 1 below provides the values of $R_{lmask}$ according to the selected MaskLeakType.

TABLE 1

Values of $R_{lmask}$ According to the Selected MaskLeakType.

| MaskLeakType | $R_{lmask}$ (cm H$_2$O)/lps$^2$ |
|---|---|
| 1 | 1420 |
| 2 | 52 |
| 3 | 37 |
| 4 | 24 |
| 'other' | 1 (Dummy value) |

According to an embodiment, $K_{2port}$ (cm H$_2$O/lps$^2$), $K_{1port}$ (cm H$_2$O/lps) and $C_{Tcal}$ (liters/cm H$_2$O) are all measured during the patient circuit calibration procedure before breath delivery starts. For useful output the estimates are filtered and scaled to units of lpm.

First order filters are utilized to filter non-useful high frequency signal and to scale the flow in units of lpm. The general continuous time (LaPlace) form of this filter is:

$$y(s) = \frac{as+b}{cs+d}x(s) \quad (20)$$

and the continuous filter is approximated using any of the discrete time substitutions, and in this particular embodiment, Tustin's bilinear transformation:

$$\frac{2}{\Delta T}\frac{z-1}{z+1} \to s \quad (21)$$

TABLE 2

Filtered Flow Definitions for NIV

| Lung flow | Total leak Flow | Port leak Flow | Mask leak Flow |
|---|---|---|---|
| x(n) = $\hat{Q}_L$(n) | x(n) = $\hat{Q}_l$(n) | x(n) = $Q_{Lport}$(n) | x(n) = $Q_{Lmask}$(n) |
| a = 0.0 | a = 0.0 | a = 0.0 | a = 0.0 |
| b = 1.0 | b = 1.0 | b = 1.0 | b = 1.0 |
| c = 0.005 sec | c = 0.005 sec | c = 0.005 sec | c = 0.005 sec |
| d = 1.0 | d = 1.0 | d = 1.0 | d = 1.0 |
| $\Delta T$ = 0.001 sec | $\Delta T$ = 0.001 sec | $\Delta T$ = 0.001 sec | $\Delta T$ = 0.001 sec |
| $\hat{Q}_{LNIV}$(n) = 60y(n) | $\hat{Q}_{ltotal}$(n) = 60y(n) | $Q_{lport}$(n) = 60y(n) | $Q_{lmask}$(n) = 60y(n) |

According to an embodiment, when either standby, circuit disconnect, or emergency ventilation conditions occur, $Q_{Lreset}$ can be set. This flag resets or holds the estimator functions at their initial conditions until breath delivery is restored. Reset affects the core estimator, the unknown leak compensation controls, and the net lung volume calculations and is used to suspend estimation when either inlet flows or proximal pressure measurements can no longer be obtained, or where the system determines the circuit model behavior has been compromised.

$$Q_{Lreset}(n) = \text{NIVStandby}(n) \text{ OR NIV\_Circ\_Disconnect}(n) \quad (22)$$

In the event that proximal pressure can no longer be measured (e.g. from a sense line disconnect), algorithms can be used to sense this condition, and in that case substitute an alternate proximal pressure estimate that can substitute for the measurement based on the inlet circuit flow, the machine pressure measurement and a calibrated model of the tubing flow resistance.

According to an embodiment, the unknown leak compensation controller determines the leak correction factor, $K_L(n)$. The action of the leak correction factor on the core estimator minimizes bias in the airway flow estimate, $\hat{Q}_L(n)$ by scaling the unknown leak estimate. This scaling action persists as long as a non-zero bias is sensed. In the non-quiescent breath state where the patient is actively breathing and pressure and flow are not flat, the leak correction factor is updated at the start of every breath according to net breath volume.

But if the breath is in the quiescent state and the airway flow bias is not near zero, bias correction is updated at every time step to rapidly drive the bias to zero. And after a fast bias correction maneuver occurs on the current breath, bias correction by net volume is suspended for the subsequent breath since the volume of the current breath will be in error (due to the fast bias correction maneuver).

For example, at step 874 of the method depicted in FIG. 8B, the system determines whether the breath is in a quiescent state. According to an embodiment, the system determines that the breath is in the quiescent state and de-biasing is appropriate if each of the following criteria are satisfied: (1) the ventilator phase is exhalation; (2) the magnitude of the airway flow estimate is >3 lpm; (3) the proximal pressure is flat; and (4) the ventilator flow is flat. If those conditions are satisfied, then the system determines that the breath is in a quiescent state, and a de-biasing can occur.

The quiescent breath state is indicated by the logical flag, $\mathcal{F}_{fast}$, calculated at every control step, n. The flag indicates that the patient has finished exhaling, and the breath is in an expiratory 'dwell' state. In this state the patient is expected to start another breath, but for the time being, both pressure and flow are flat. The quiescence state is furthermore restricted to an airway bias flow that is away from zero; its magnitude is some threshold about zero. Flatness for the signals involved is determined by using a heavily filtered derivative of the signals.

Using the filtered derivative, the magnitudes of the rate of change for proximal pressure and net flow are determined.

For the magnitude of the rate of change of net flow, $\dot{Q}_{netAbs}(n)$, $x(n) = Q_b(n) + Q_{O2}(n)$:

$$\dot{Q}_{netAbs}(n) = |y(n)| \quad (34)$$

where $\omega_o = 2\pi$ rad/sec, $\zeta = 0.707$, and $\Delta T = 0.001$ sec, according to an embodiment. For the magnitudes of the rate of change of proximal pressure, $\dot{P}_{proxAbs}(n)$, $x(n) = P_{prox}(n)$:

$$\dot{P}_{proxAbs}(n) = |y(n)| \quad (35)$$

where $\omega_o = 2\pi$ rad/sec, $\zeta = 0.707$, and $\Delta T = 0.001$ sec, according to an embodiment. For the magnitudes of the rate of change of lung flow estimate, $\dot{Q}_{LhatAbs}(n)$, $x(n) = \hat{Q}_{LNIV}(n)$:

$$\dot{Q}_{LhatAbs}(n) = |y(n)|$$

where $\omega_o = 2\pi$ rad/sec, $\zeta = 0.707$, and $\Delta T = 0.001$ sec, according to an embodiment.

The flag that determines the quiescent breath state, $\mathcal{F}_{fast}(n)$ is then determined by the following latch function:

$$\mathcal{F}_{fast}(n) = \begin{cases} 1 & \text{rising edge of} \begin{bmatrix} \begin{pmatrix} (\dot{Q}_{netAbs}(n) < 1.0) \text{ AND} \\ (\dot{P}_{proxAbs}(n) < 0.5) \text{ AND} \\ |\hat{Q}_{LNIV}(n)| > 3.0 \text{ AND} \\ \overline{IE} \end{pmatrix} \end{bmatrix} \text{ for 300 msec} \\ 0 & \text{rising edge of} \begin{bmatrix} \begin{pmatrix} (\dot{Q}_{LhatAbs}(n) < 1.0) \text{ AND} \\ |\hat{Q}_{LNIV}(n)| < 2.0 \end{pmatrix} \\ \text{OR} \\ IE \end{bmatrix} \text{ for 300 msec} \end{cases} \quad (36)$$

While $\mathcal{F}_{fast}(n)$ is TRUE, the shape component for breath trigger in the system shall be inhibited. Processing of the shape trigger calculations are not suspended during $\mathcal{F}_{fast}(n)$ TRUE, just the invocation of trigger from shape processing. This allows the fast de-bias process to complete. For the output of airway flow estimate in NIV, $Q_{Lung\_dry}(n) = \hat{Q}_{LNIV}(n)$, $Q_{Lung\_dry}(n)$ shall be converted to the BTPS reference frame according to the conversion formula.

EXAMPLE

Estimator Calculations

According to an embodiment, quiescent state can be represented by the flag $\mathcal{F}_{fast}(n)$ and the bias correction inhibit flag, $\mathcal{F}_{inh}(n)$ which is described by the following latch function that additionally controls the 'clocking' of the controller.

$$\mathcal{F}_{inh}(n) = \begin{cases} 1 & \text{on the rising edge of } \mathcal{F}_{fast}(n) \\ 0 & \text{at the start of exhalation} \end{cases} \quad (23)$$

$$K_L(n) = \begin{cases} \min\{\max\{[K_{Liln}(k) + K_L(k-1)], K_{Lmin}\}, K_{Lmax}\} & \text{for } (\mathcal{F}_{fast}(n) = 0) \text{ AND}(\mathcal{F}_{in}(n) = 0) \\ K_L(k-1) & \text{for } (\mathcal{F}_{fast}(n) = 0) \text{ AND}(\mathcal{F}_{in}(n) = 1) \\ \min\{\max\{[K_{Liln}(n) + K_L(n-1)], K_{Lmin}\}, K_{Lmax}\} & \text{for } \mathcal{F}_{fast}(n) = 1 \end{cases} \quad (24)$$

The input to the compensator (integrator) is:

$$K_{Lih}(n) = \beta \tilde{Q}_m(n) \tag{25}$$

$$K_{Lih}(n) = \begin{cases} \beta \tilde{Q}_m(StartOfInh) & \text{for } (\mathcal{F}_{fast}(n) = 0) \text{ AND } (\mathcal{F}_{in}(n) = 0) \\ K_{Lih}(EndOfLastExhalation) & \text{for } (\mathcal{F}_{fast}(n) = 0) \text{ AND } (\mathcal{F}_{in}(n) = 1) \\ \beta \tilde{Q}_m(n) & \text{for } \mathcal{F}_{fast}(n) = 1 \end{cases}$$

where, according to an embodiment, $K_{Lmax}=5.0$; $K_{Lmin}=-5.0$; $\beta=1.0$; and $K_L(0)=0.0$. These calculations should be interpreted as follows: controls are either updated on a breath to breath basis or at every time step according to the size and flatness of the bias. And a breath to breath update is suspended if a fast bias adjustment occurred on the previous breath.

EXAMPLE

Integration of Estimated Airway Flow and Determination of the Airway Flow Bias Metric According to an embodiment, the following obtains the net breath volume:

$$V_{Linst}(n) = \tag{26}$$

$$\begin{cases} 0.001 & \text{if } (StartOfInh(n-1) == 1) \text{ OR} \\ & (Q_{Lreset} == 1) \text{ OR } (\mathcal{F}_{fast}(n) == 1) \\ \Delta T \dfrac{\hat{Q}_{LNIV}(n)}{60} + V_{Linst}(n-1) & \text{otherwise} \end{cases}$$

This says that the net breath volume calculation is reset one step after the start of inhalation (a one clock event) or otherwise held in reset during a fast bias correction maneuver. And the net volume is latched at the start of inhalation:

$$V_L(k) = V_{L\ inst}(n) \text{ if } StartOfInh(n)==1 \tag{27}$$

From the net breath volume obtain the mean breath flow by dividing net breath volume by the breath duration:

$$\overline{Q}_L(k) = \frac{V_L(k)}{T_B(k)} \tag{28}$$

next determine the mean (actual) breath pressure:

$$\Sigma P_{prox\ Inst}(n) = \tag{29}$$

$$\begin{cases} 0.001 & \text{if } (StartOfInh(n-1) == 1) \text{ OR} \\ & (Q_{Lreset} == 1) \text{ OR } (\mathcal{F}_{fast}(n) == 1) \\ \Delta T P_{prox}(n) + \Sigma P_{prox\ Inst}(n-1) & \text{otherwise} \end{cases}$$

$$\Sigma P_{prox}(k) = \Sigma P_{prox\ Inst}(n) \text{ if } StartOfInh(n) == 1 \tag{30}$$

and the average pressure over the breath is:

$$\overline{P}_{prox}(k) = \frac{\Sigma P_{prox}(k)}{T_B(k)} \tag{31}$$

Normalization and linearization is required to maintain a constant loop gain despite specific breath timing, pressure or leak differences. The ratio of expected average pressure to actual average pressure, neglecting the linear term accomplishes this, with only minor affine shift. This ratio, considering the quadratic reduces to the dimensionless bias metric:

$$\tilde{Q}_l(k) = \frac{\tilde{Q}_L(k)}{\min\limits_{60\ \text{sec}} \dfrac{\sqrt{K_1^2 + 4K_2 \max\{\overline{P}_{prox}(k), 0.1\}} - K_1}{2K_2}} \tag{32}$$

$$\tilde{Q}_m(n) = \begin{cases} \tilde{Q}_l(k) & \text{if } \mathcal{F}_{fast}(n) == 0 \\ \Delta T K_{debias} \hat{Q}_{LNIV}(n) & \text{if } \mathcal{F}_{fast}(n) == 1 \end{cases} \tag{33}$$

$K_{debias} = 1.0$

Experimental Results

Figure 10:
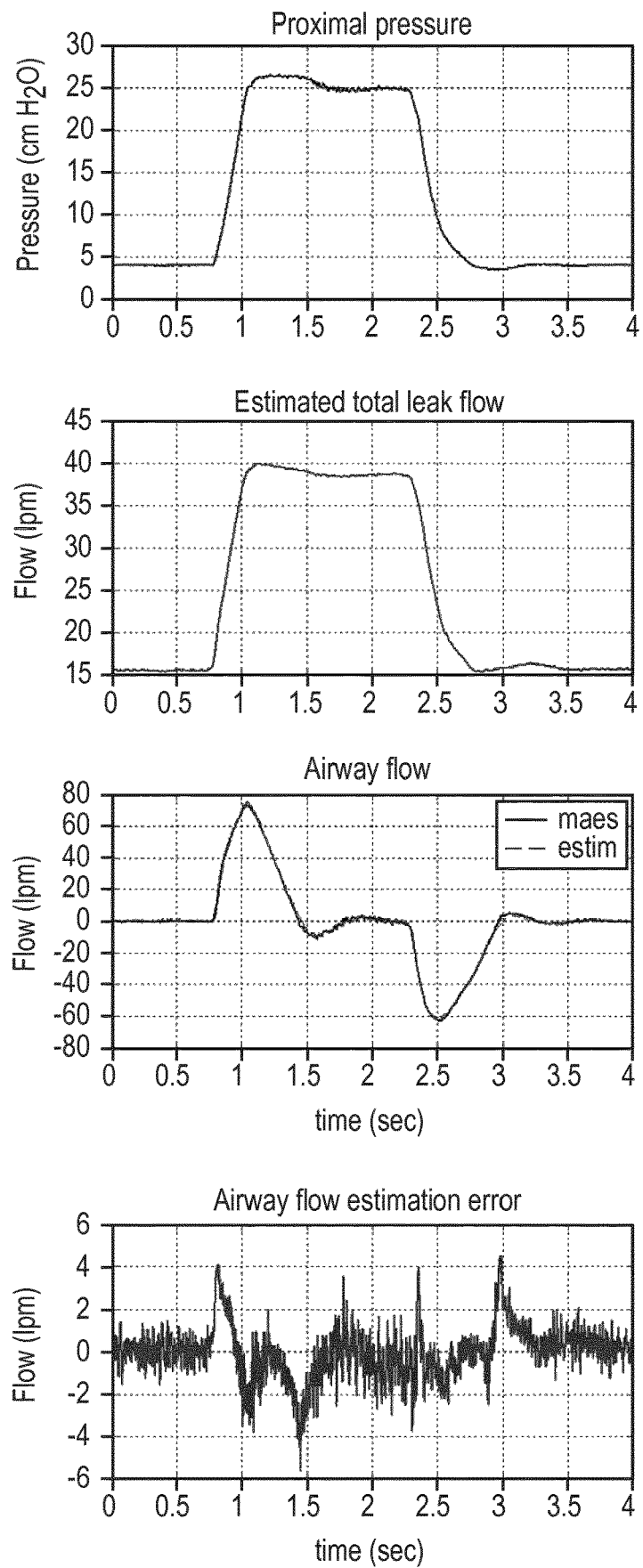
FIG. 10 is a series of graphs for proximal pressure, estimated total leak flow, airway flow, and airway flow estimation error, in accordance with an embodiment.
Figure 11:
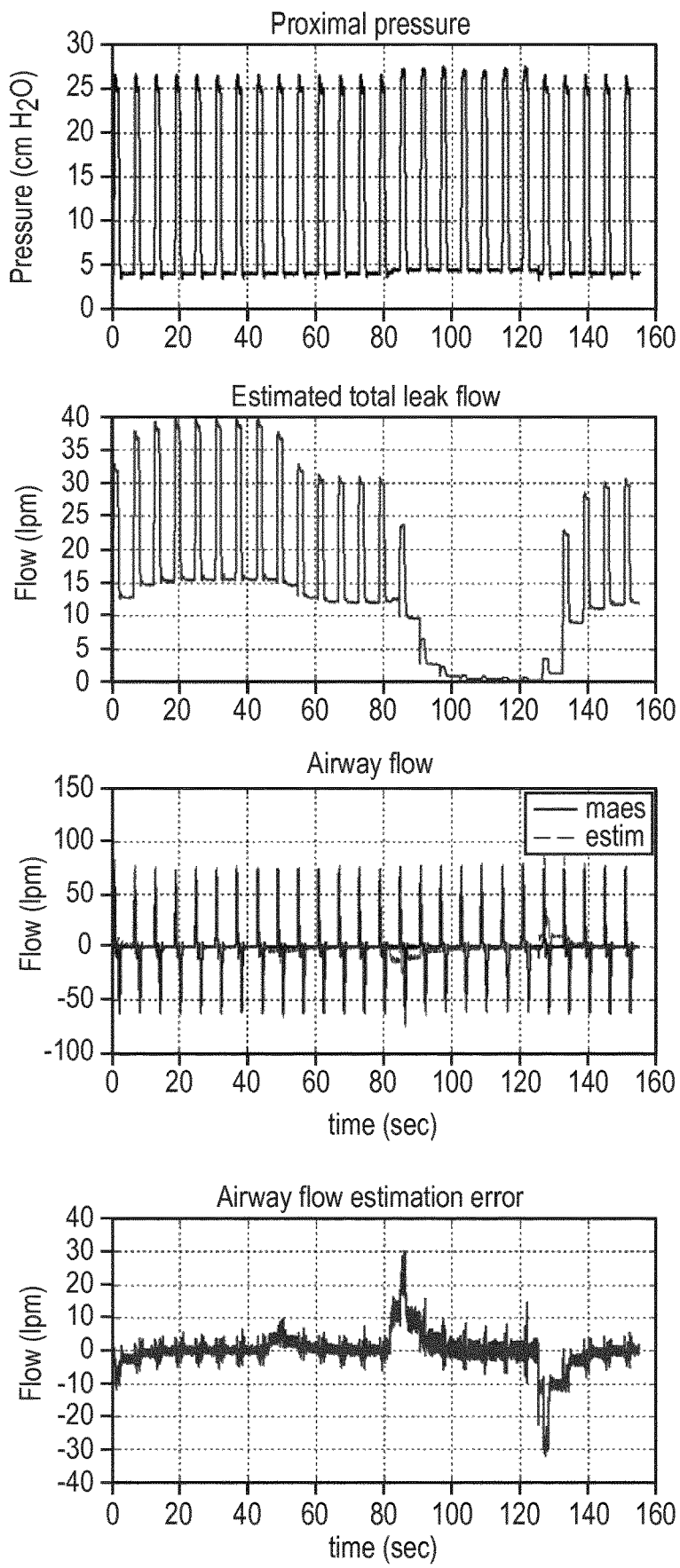
FIG. 11 is a series of graphs for proximal pressure, estimated total leak flow, airway flow, and airway flow estimation error, in accordance with an embodiment.

According to one embodiment, the estimator method and system was built using Simulink software and subsequently specified for software implementation in an NIV product. An example single breath pressure and flow waveforms ventilating a Michigan Instruments Training and Test Lung are shown in FIG. 10. Lung compliance was set to about 0.02 liters/cm H$_2$O and an Rp5 airway restriction was used. A Respironics 22 mm BiPAP circuit with DEP exhalation port leak was used. Circuit compliance was calibrated at 0.0008 liters/cmH$_2$O and the known leak as 97 cm H$_2$O/(1/sec)^2. A measured lung flow error of about 1.5 lpm rms was achieved with peak errors on breath transition of less than 6 lpm. FIG. 11 illustrates a series of breaths. A sudden unknown leak step change is introduced in the circuit connection after the first breath (~5 sec). The leak is then removed at 50 seconds. At 85 seconds the known leak is almost fully occluded. From these series of disturbing actions the total leak estimate responds and the airway flow estimate (dashed line) rapidly recovers within a few breaths.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for estimating patient airway flow in a non-invasive ventilator system, the method comprising the steps of:

providing a non-invasive ventilator system, the ventilator system comprising tubing having a distal, ventilator end and a proximal, patient end;

obtaining a measurement of tubing compliance and a measurement of one or more parameters of an exhalant port leak flow model of the non-invasive ventilator system;

measuring, using a distal gas flow sensor of the non-invasive ventilator, gas flow at the distal end of the tubing;

measuring, using a proximal pressure sensor of the non-invasive ventilator, pressure at the proximal end of the tubing;

determining an estimated pressure at the proximal end of the tubing, the estimated pressure comprising the measurement of gas flow at the distal end of the tubing, the measurement of pressure at the proximal end of the tubing, the obtained measurement of tubing compliance, and the obtained measurement of one or more parameters of the leak flow model;

determining a proximal pressure estimate error value by subtracting the measured pressure at the proximal end of the tubing from the estimated pressure at the proximal end of the tubing;

compensating, using a compensator, for the determined proximal pressure estimate error value;

compensating for an error in the estimated pressure at the proximal end of the tubing by feeding that estimate back into a sum of accumulated flows;

determining an estimated gas flow leak, the estimated gas flow leak comprising the estimated pressure at the proximal end of the tubing and the obtained measurement of one or more parameters of the leak flow model;

monitoring, on a breath to breath basis, for an unknown leak in the non-invasive ventilator system;

determining, when the unknown leak is identified, a gas flow leak factor;

adjusting, with the determined gas flow leak factor, the estimated gas flow leak, in order to reduce an airway flow estimate bias on a breath by breath basis;

detecting a bias on the airway flow estimate;

determining that the system is within a quiescent state of a breath;

de-biasing, only if the system is in the quiescent state, the estimated gas flow leak factor in order to drive the detected bias to approximately zero; and suspending bias correction on an immediately subsequent breath.

2. The method of claim 1, wherein the step of determining that the system is within the quiescent state comprises determining that the breath is in an exhalation phase, that the airway flow estimate is greater than 3 1 pm, that the measured proximal pressure is constant, and that the measured gas flow is constant.

3. The method of claim 1, wherein the de-biasing occurs in less than 300 milliseconds.

4. The method of claim 1, wherein the step of obtaining a measurement of tubing compliance and a measurement of the one or more parameters of the leak flow model comprises one or more calibration measurements.

5. The method of claim 1, further comprising the step of comparing the gas flow leak factor to a predetermined lower limit.

6. The method of claim 5, wherein an alarm is triggered if the gas flow leak factor is below the predetermined lower limit.

7. The method of claim 1, further comprising the step of comparing the gas flow leak factor to a predetermined upper limit.

8. A non-invasive ventilator system comprising:
airway tubing comprising a distal, ventilator end and a proximal, patient end; a distal gas flow sensor configured to measure gas flow at the distal end of the tubing; a proximal pressure sensor configured to measure pressure at the proximal end of the tubing; and a gas flow controller configured to supply a determined volume of gas to the distal end of the tubing, wherein the gas flow controller is configured to determine the supplied volume of gas by: (i) determining an estimated pressure at the proximal end of the tubing, the estimated pressure comprising a measurement of gas flow at the distal end of the tubing, a measurement of pressure at the proximal end of the tubing, a measurement of tubing compliance, and a measurement of one or more parameters of a leak flow model; (ii) determining a proximal pressure estimate error value by subtracting a measured pressure at the proximal end of the tubing from the estimated pressure at the proximal end of the tubing; (iii) compensating for the determined proximal pressure estimate error value; (iv) compensating for an error in the estimated pressure at the proximal end of the tubing by feeding that estimate back into a sum of accumulated flows; (v) determining an estimated gas flow leak, the estimated gas flow leak comprising the estimated pressure at the proximal end of the tubing and the obtained measurement of one or more parameters of the leak flow model; (vi) monitoring on a breath by breath basis for an unknown leak in the non-invasive ventilator system; (vii) determining, when the unknown leak is identified, a gas flow leak factor; (viii) adjusting, with the determined gas flow leak factor, the estimated gas flow leak, in order to reduce an airway flow estimate bias on a breath by breath basis; (ix) detecting a bias on the airway flow estimate; (x) determining that the system is within a quiescent state of a breath; (xi) de-biasing the estimated gas flow by adjusting the leak factor in order to drive the detected bias to approximately zero; and (xii) suspending bias correction on an immediately subsequent breath.

9. The non-invasive ventilator system of claim 8, wherein the system is within the quiescent state of the breath if the breath is in an exhalation phase, if the airway flow estimate is greater than 3 1 pm, if the measured proximal pressure is constant, and if the measured gas flow is constant.

10. The non-invasive ventilator system of claim 8, wherein the de-biasing occurs in less than 300 milliseconds.

11. The non-invasive ventilator system of claim 8, wherein the controller comprises a compensator configured to compensate for the determined proximal pressure estimate error value.

12. The non-invasive ventilator system of claim 8, wherein the controller is further configured to compare the gas flow leak factor to a predetermined lower limit.

13. The non-invasive ventilator system of claim 12, wherein the controller is further configured to trigger an alarm if the gas flow leak factor is below the predetermined lower limit.

14. The non-invasive ventilator system of claim 12, wherein the controller is further configured to compare the gas flow leak factor to a predetermined upper limit.

15. The non-invasive ventilator system of claim 12, wherein the controller is further configured to trigger an alarm if the gas flow leak factor is above a predetermined upper limit.

* * * * *